United States Patent [19]
Weyenberg

[11] Patent Number: 5,359,525
[45] Date of Patent: Oct. 25, 1994

[54] APPARATUS AND METHOD FOR REGISTRATION CONTROL OF ASSEMBLED COMPONENTS

[75] Inventor: Steven L. Weyenberg, Appleton, Wis.

[73] Assignee: Kimberly-Clark Corporation, Neenah, Wis.

[21] Appl. No.: 517,568

[22] Filed: May 1, 1990

[51] Int. Cl.$^5$ .................................. G06F 15/46
[52] U.S. Cl. .................. 364/469; 356/429; 356/431
[58] Field of Search ............. 364/468, 469, 470, 471, 364/473; 356/429, 430, 431; 156/64, 350, 351, 354, 378, 379, 522; 83/74, 358, 365, 520, 521; 250/571, 572

[56] References Cited

U.S. PATENT DOCUMENTS

| | | | |
|---|---|---|---|
| 4,166,541 | 9/1979 | Smith, Jr. ........................ | 356/431 |
| 4,237,539 | 12/1980 | Piovoso et al. .................. | 364/552 |
| 4,322,752 | 3/1982 | Bixby ............................... | 358/213 |
| 4,330,846 | 5/1982 | Colles et al. .................... | 364/900 |
| 4,680,205 | 7/1987 | Lerner et al. .................... | 428/29 |
| 4,719,575 | 1/1988 | Gnuechtel ......................... | 364/469 |
| 4,816,052 | 3/1989 | Horvath ............................ | 364/473 |
| 4,837,715 | 6/1989 | Ungpiyakul et al. ............. | 364/552 |
| 5,235,515 | 8/1993 | Ungpiyakul et al. ............. | 364/469 |

Primary Examiner—Joseph Ruggiero
Assistant Examiner—Thomas E. Brown
Attorney, Agent, or Firm—Thomas M. Gage; Thomas J. Mielke

[57] ABSTRACT

Registration inspection of composite products during the fabrication of a series of such products is accomplished by making a two-dimensional image of a product and analyzing the image to determine the location of at least one component in the machine direction and the location of at least one component in the transverse direction. The thus determined locations are compared to the desired locations for the respective components in the composite article, and feedback control signals are utilized to adjust the fabrication process so that the components will be at the desired locations in subsequent products. When a component is outside of its acceptable position, the article can be removed from the fabrication line without further processing. The invention is particularly useful with fabrication lines for the production of absorbent articles, such as disposable diapers, incontinence devices, sanitary napkins, and the like.

18 Claims, 3 Drawing Sheets

APPARATUS AND METHOD FOR REGISTRATION CONTROL OF ASSEMBLED COMPONENTS

FIELD OF THE INVENTION

The present invention relates to a method and apparatus for sequentially inspecting composite products in a plurality of such products moving in series in a fabrication line to determine the location of selected component elements within each inspected product and to adjust the fabrication of subsequent products so as to maintain the location of the selected component elements in subsequent products within acceptable ranges.

BACKGROUND OF THE INVENTION

Various products are fabricated in a continuous production line by the sequential addition of components to previously supplied components. This is particularly advantageous when one or more of the components can be supplied in the form of a continuous sheet or web. Thus, in the formation of disposable absorbent articles such as diapers, incontinence devices, sanitary napkins, and the like, the liquid impermeable outer layer is normally supplied at a point in the fabrication line in the form of a continuous roll of plastic film and the liquid permeable inner liner can be supplied at another point in the fabrication line in the form of a continuous roll of non-woven fabric, while absorbent pads, waist elastic bands, leg elastic bands, and/or other elements can be supplied at different points in the fabrication line as discrete objects. While the outer layer and the inner liner can, but need not, be coextensive in their dimensions, both in the machine direction and in the transverse direction, the dimensions of most if not all of the other components represent only a fraction of the dimensions of the outer layer. Thus, it is necessary to provide some means for bringing the various components of a single composite product together so that the components in the composite product are in proper registration with respect to each other. However, variations in the components or in the operating environment can cause components to be mispositioned or even omitted from a particular composite product. Mispositioned or missing elements can degrade the quality of the composite product or even render the composite product unsuitable for its intended purpose.

While the in-process products can be inspected manually or automatically at various stages along the fabrication line, an ineffective or inaccurate inspection may not maintain the composite product within its design specifications and/or may not efficiently and accurately cull out the unacceptable composite products. Unnecessary shut-downs of the fabrication line reduce production efficiency and increase product costs.

Various methods and apparatuses have been developed for the purpose of inspecting composite products which are fabricated from at least one moving web. For example, U.S. Pat. No. 4,837,715 to Ungpiyakul et al., issued Jun. 6, 1989 to Kimberly-Clark Corporation, discloses an apparatus for determining the relative locations of selected components within a product segment of a moving web. Photoelectric detectors can be mounted at a plurality of locations along the machine direction length of the composite product fabrication equipment whereby the relative locations of components in the machine direction can be determined. Optical brighteners can be incorporated into various components of the composite product being formed from a web, in order to facilitate detection of selected components utilizing an ultraviolet light source. A plurality of photoelectric detectors can be disposed serially along the machine direction in order to detect the location of different selected elements, and the resulting output signals can be stored for subsequent association with other measurement signals for the same individual product.

U.S. Pat. No. 4,680,205 to Lerner et al., issued Jul. 14, 1987, discloses the use of electromagnetic radiation shifting indicia incorporated into a component of a composite being formed from a web in order to facilitate detection of the component. If such component is covered up during the fabrication process, an additional component having the radiation shifting indicia can be added to the product. Only those elements of the web in which the shifting indicia is incorporated will be activated by ultraviolet light to produce visible light. The presence or absence of the thus produced visible light can be detected by photoelectric detectors as an indication of the presence and position of the selected component. A series of photoelectric detectors can be disposed serially along the machine direction in order to detect the location of the sequentially selected components.

While such inspections systems may be satisfactory for some installations, they are particularly deficient when it is desirable to determine the registration of one or more components in the transverse direction instead of making all of the measurements in the machine direction. The machine direction is the direction in which the in-process articles move along the fabrication line, while the transverse direction is perpendicular to the machine direction. Thus, for a continuous web component, the length of the web would be in the machine direction, while the width of the web would be in the transverse direction. Such conventional apparatuses do not provide for the inspection of the registration of web components based upon their relative positions transverse to the machine direction. That is, such conventional apparatuses are able to measure the machine direction spacing between selected web components but not the transverse direction spacing.

Another problem is encountered with registration detection systems employing a plurality of sensors which are located at various points along the length of the fabrication equipment. In many composite articles produced from at least one continuous web, the continuous web component is thin and subject to stretching. Since it is virtually impossible to maintain the tension of the continuous web component constant during the various fabrication steps, the degree of stretching that the continuous web component undergoes can vary. Such stretching can cause variations in the registration of the initially deposited components with respect to subsequently deposited components or subsequent processing operations. Thus, even though an early component may be initially within its acceptable position range, the stretching of the continuous web or the jostling of the discrete components during the fabrication process may result in the early component being outside of its acceptable position range in the final composite product.

Accordingly, it is an object of the invention to provide a method and apparatus which is capable of measuring the relative positions of components of a composite article in the transverse direction or in both the machine direction and the transverse direction. It is an object of the invention to provide a more complete inspection of the positional relationships of components in a composite article, particularly in such an article produced from at least one continuous web. It is an object of the present invention to conduct, at a single location in the fabrication process, an inspection of the positional relationship of components in a composite article. It is another object of the invention to perform rapid analyses of web sections as they pass along the machine direction of the fabrication equipment. A further object of the invention is to provide for feedback control of the operation of the fabrication equipment to maintain the product specifications within acceptable ranges. An additional object of the invention is to provide improved means to cull any defective products. Another object of the present invention is to at least reduce, if not eliminate, the need for human monitoring and intervention in the fabrication process.

SUMMARY OF THE INVENTION

The apparatus and method of the present invention provide for registration inspection of a composite article at a downstream point in the fabrication equipment using a single image detector which is capable of producing a two-dimensional image of the composite article and evaluating at least portions of the two-dimensional image to determine the positional relationship of components of the composite article in the transverse direction. The invention can provide for the determination of the positional relationships of components both in the transverse direction and in the machine direction of the fabrication equipment. The thus determined positional relationships can be compared to the desired positional relationships and signals representing the deviation of the actual positional relationship from the desired positional relationship can be used in a feedback control to adjust the operation of the respective component supply means in order to maintain the position of that component in each article within its acceptable range. The feedback control can also remove defective articles from the fabrication line without further processing, thereby providing improved quality control with respect to the articles produced.

The inspection apparatus of the present invention includes an image-producing means and an image analyzing means. The image-producing means creates an instantaneous two-dimensional image of a composite article as it passes through the inspection station in the fabrication process. The resulting image is conveyed to the image analyzing means which analyzes at least portions of the image to compare the actual positional relationships of selected components of the composite article to the desired positional relationships for the respective components. The image-analyzing means produces an output signal in response to the differential result of each such comparison. Each output signal which indicates an undesirable deviation is then directed to feedback control means to regulate the supply of the respective component to the fabrication system, thereby correcting the fabrication process.

BRIEF DESCRIPTION OF THE DRAWINGS

A more complete understanding of the present invention, its objects, and its advantages will be apparent from the following detailed description read in conjunction with the accompanying drawings in which.

DETAILED DESCRIPTION

Figure 1:
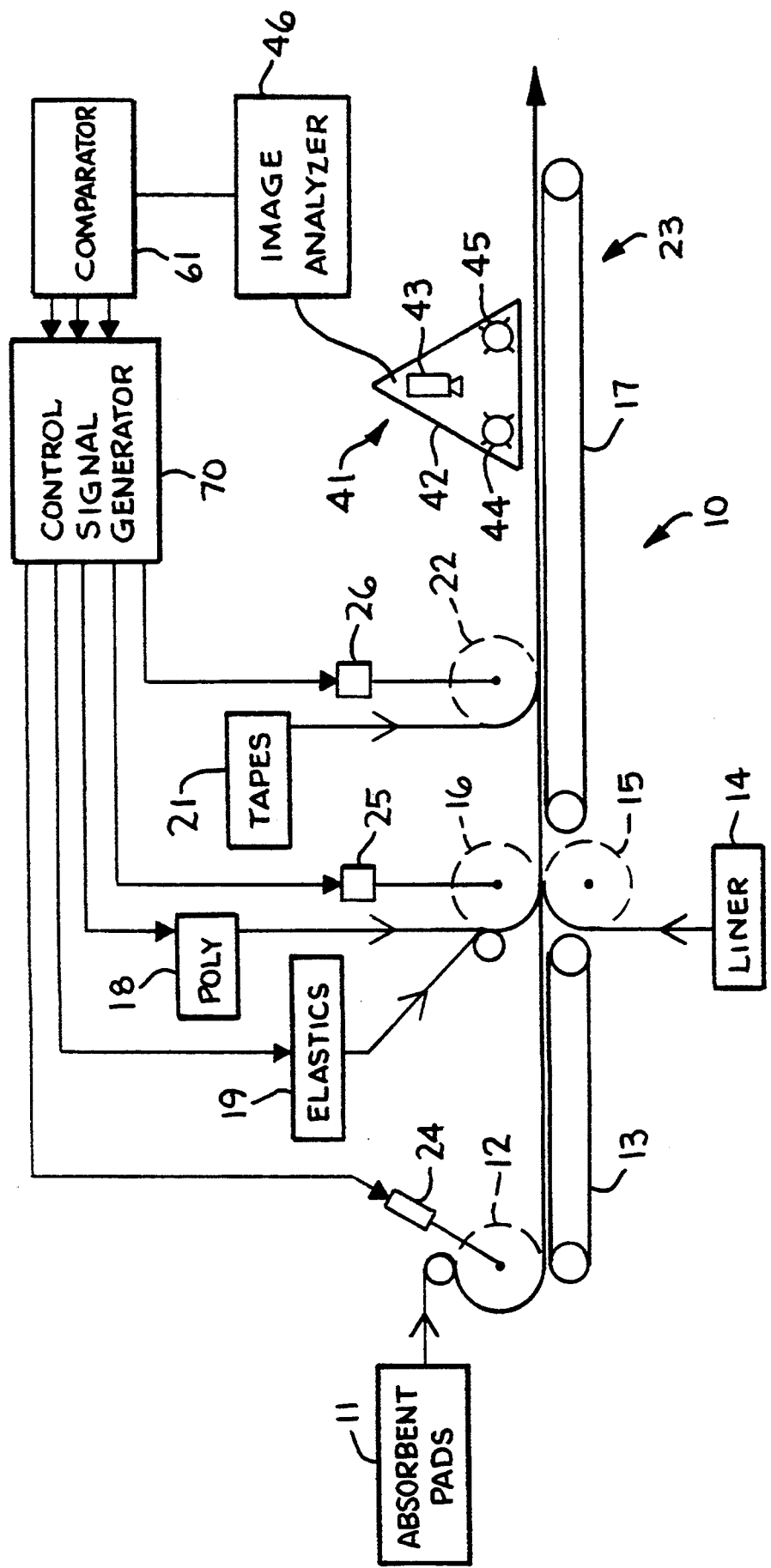
FIG. 1 is a schematic presentation of a first embodiment of a fabrication line incorporating the registration inspection apparatus of the present invention.

While the invention is applicable to the production of composite articles from only discrete components, it is particularly advantageous for the production of composite articles which are formed from at least one continuous sheet or web. Accordingly, for purposes of illustration, it will be described in terms of a fabrication line for producing discrete absorbent articles from a continuous outer layer sheet, a continuous liner sheet, and discrete components such as elastic bands, tapes, and absorbent pads. An absorbent article fabrication line including apparatus for inspecting the registration of various components in the resulting composite absorbent article is generally indicated at 10 in FIG. 1. Individual absorbent pads are withdrawn from a source 11 thereof and passed by suitable conveying means including a drive roll 12 and a first fabrication line conveyor 13. Liner fabric in the form of a continuous web of non-woven fabric is withdrawn form a source 14 thereof, passed between a pair of nip rolls 15 and 16, and then conveyed along second fabrication line conveyor 17. The outer layer in the form of a continuous sheet of plastic film is withdrawn from a source 18 thereof, while individual elastic bands are withdrawn from a source 19 thereof and are sequentially combined with the plastic film. The absorbent pads leave the first fabrication line conveyor 13 and are deposited on the liner fabric upstream of the nip rolls 15 and 16. The combination of plastic film and elastic bands also passes between the nip rolls 15 and 16, with the absorbent pads being positioned between the liner fabric and the plastic sheet having the elastic bands thereon. The resulting in-process web is transferred from the nip rolls 15 and 16 to the second fabrication line conveyor 17. Individual tapes are withdrawn from a source 21 thereof and added to the existing in-process web, and the resulting new in-process web passes along conveyor 17 and beneath applicator roll 22. The resulting composite web travels along the machine direction of the fabrication line 10 and proceeds through an inspection station 23. The fully assembled composite web can be severed transversely at periodic intervals to form a plurality of discrete absorbent articles, such as the incontinence device illustrated in FIG. 2. However, it is to be appreciated that apparatus 10 can be utilized effectively with respect to the production of other composite articles. The severance of the continuous web into discrete composite articles can be effected either prior to or subsequent to the inspection station 23.

Each segment of an in-process continuous web which will become a discrete article can be considered to be an in-process article. Thus as the in-process web passes through the fabrication steps, various components are applied to the web to form a new in-process article until all of the components have been added, thereby forming the fully assembled composite web. The exact order of addition can vary with the type of article or with the design of the particular article. Thus the elastic bands can be added directly to the liner material rather than directly to the outer layer sheet, or they can be added individually to the in-process web. The relative position of the absorbent pad in an article is determined, at least primarily, by motor 24 driving roll 12 in synchronization with the motor 25 which drives nip roll 15 and the rate at which the liner material is withdrawn from its source 14. The tapes are applied to the in-process web by applicator roll 22 in an intermittent manner. Thus, the relative position of the tapes in an article is determined, at least primarily, by motor 26 driving applicator roll 22 in synchronization with nip rolls 15 and 16.

Figure 2:
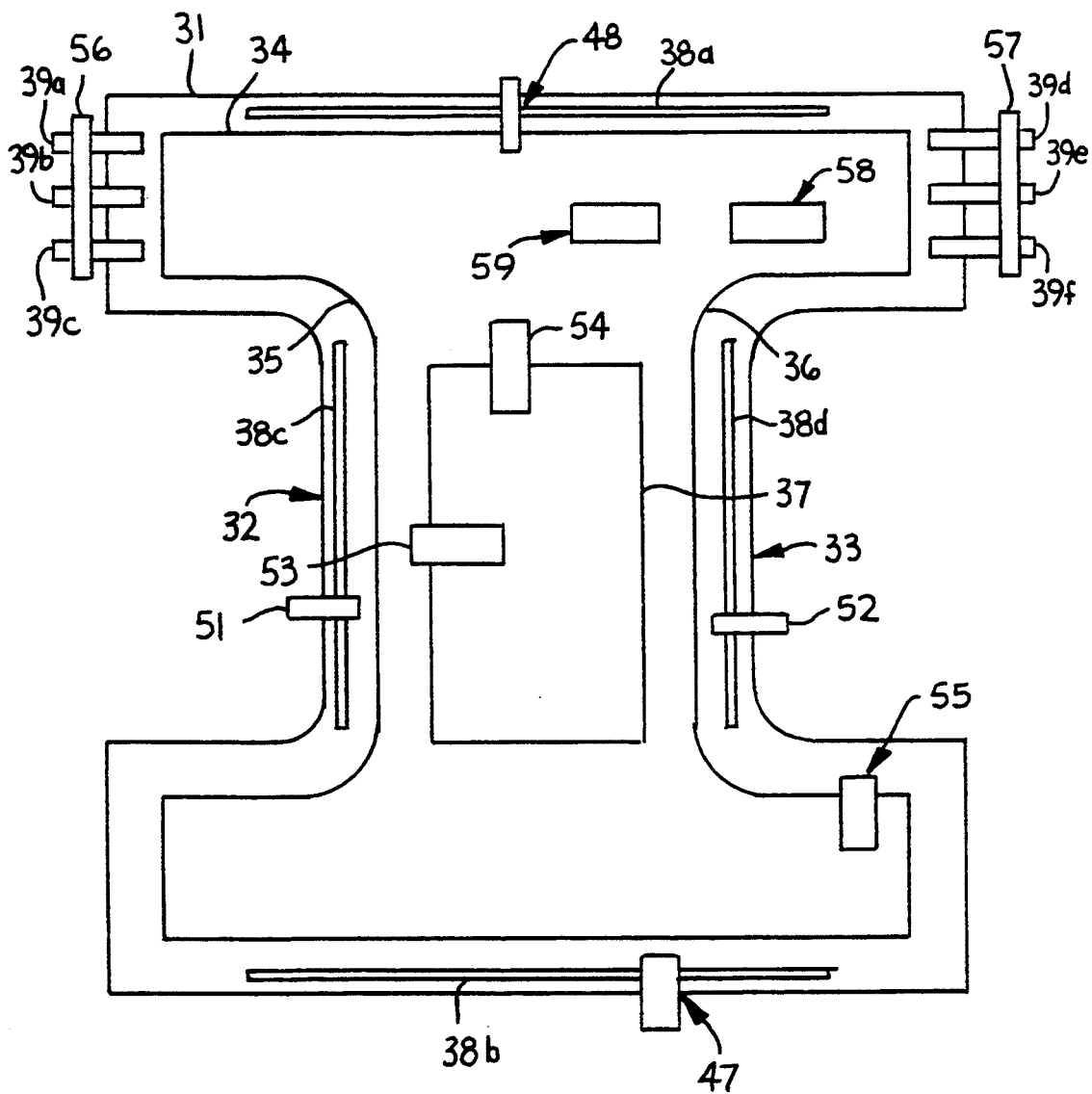
FIG. 2 is a plan view of a representative composite article which can be fabricated by the apparatus of the present invention.

The desired positional relationships of the components of a single fully assembled composite article which can be employed as an incontinence device is depicted in FIG. 2. The orientation of this article during fabrication can be such that the machine direction of the fabrication line extends from the top of FIG. 2 downwardly to the bottom of FIG. 2. The lining fabric has been omitted from this illustration for purposes of simplicity. The plastic outer sheet 31 is in the form of a rectangle with leg cut-outs 32 and 33. The absorbent 34 is in the form of a smaller rectangle, also having leg cut-outs 35 and 36. The absorbent pad has a thicker crotch section 37 which can be in the form of a thicker portion which is produced during the manufacture of the absorbent pad or in the form of a separate absorbent pad which is added during the fabrication of the incontinence device. Elastic bands 38 include waist elastics 38a and 38b and leg elastics 38c and 38d. Tapes 39 include right side (viewed facing in the machine direction) tapes 39a, 39b, and 39c and left side (viewed facing in the machine direction) tapes 39d, 39e, and 39f.

Following the application of tapes 39, the fully assembled composite web passes through inspection station 23. Registration inspection apparatus 41 is located at the inspection station 23 and comprises a housing 42 containing a camera 43 and light sources 44 and 45. The bottom of the housing 42 is transparent to the light emitted by light sources 44 and 45 and to the light to be detected by the camera 43. Camera 43 can be any suitable type of video camera which is capable of creating a two-dimensional image of a single composite article located beneath it at the inspection station 23. For example, camera 43 can be a high shutter speed camera having a matrix of photodiodes disposed therein whereby the matrix of photodiodes electronically produces a still picture image of the composite article in the inspection station 23. In the apparatus of FIG. 1, camera 43 is mounted on the same side of the composite article as the light sources 44 and 45, so that the camera 43 produces an image from the light reflected or emitted from the top of the composite article.

The image produced by camera 43 provides an electronic representation of the positional relationships of the various light reflecting components of the composite article, permitting an inspection of the presence and relative placement of the various components. This electronic image is transmitted to image analyzer 46. While it is possible to analyze the entire image, it is preferable to analyze only selected areas of the image. Thus, with regard to FIG. 2, area 47 can be analyzed to determine the machine direction position of waist elastic band 38b with respect to the leading edge of the article; area 48 can be analyzed to determine the machine direction position of the waist elastic band 38a and the trailing edge of absorbent layer 34 with respect to the trailing edge of the article; area 51 can be analyzed to determine the transverse direction position of the leg elastic band 38c with respect to inner edge of the left leg cut-out in outer layer 32; area 52 can be analyzed to determine the transverse direction position of the leg elastic band 38d with respect to inner edge of the right leg cut-out in outer layer 32; area 53 can be analyzed to determine the transverse direction position of the left edge of the thick absorbent section 37; area 54 can be analyzed to determine the machine direction position of the trailing edge of the thick absorbent section 37; area 55 can be analyzed to determine the machine direction position of the trailing edge of the leading left ear of absorbent pad 34; area 56 can be analyzed to determine the machine direction position of tapes 39a, 39b and 39c; and area 57 can be analyzed to determine the machine direction position of tapes 39d, 39e and 39f. These analyses can be accomplished by determining the location in the particular area of the electronic image where the image goes from dark to light or from light to dark, thereby indicating a component edge. Areas 58 and 59 can be utilized to determine the uniformity of the absorbent layer 34, by comparing the grayness of area 58 to the grayness of area 59.

The component positions determined by the image analyzer are transmitted to comparator 61, wherein the actual position of each analyzed component edge in the composite article being inspected is compared with the desired position for that component edge. If the position of a component is outside a predetermined tolerance range, apparatus 10 provides for a system adjustment and, if necessary, a culling of the defective product. As set forth in detail below, the web component registration inspection apparatus of the present invention provides the requisite quality control with respect to each disposable incontinent device contained in the composite web.

In one version of the embodiment of FIG. 1, light sources 44 and 45 are ultraviolet light sources and are disposed on the same side of the composite web as image-producing means 41. In this version, optical brighteners are incorporated into various components of the composite web such that the optical brighteners are activated by the ultra-violet light to produce light in the visible wavelength. Housing 42 prevents camera 43 from seeing visible light other than that emanating from the composite web. In this way, image-producing means 41 creates an image of only those components of the web which include optical brighteners. Those components of the composite web which do not contain optical brighteners do not react to the ultraviolet light to produce light at a visible wavelength and therefore will not appear in the image produced by image-producing means 41.

Figure 3:
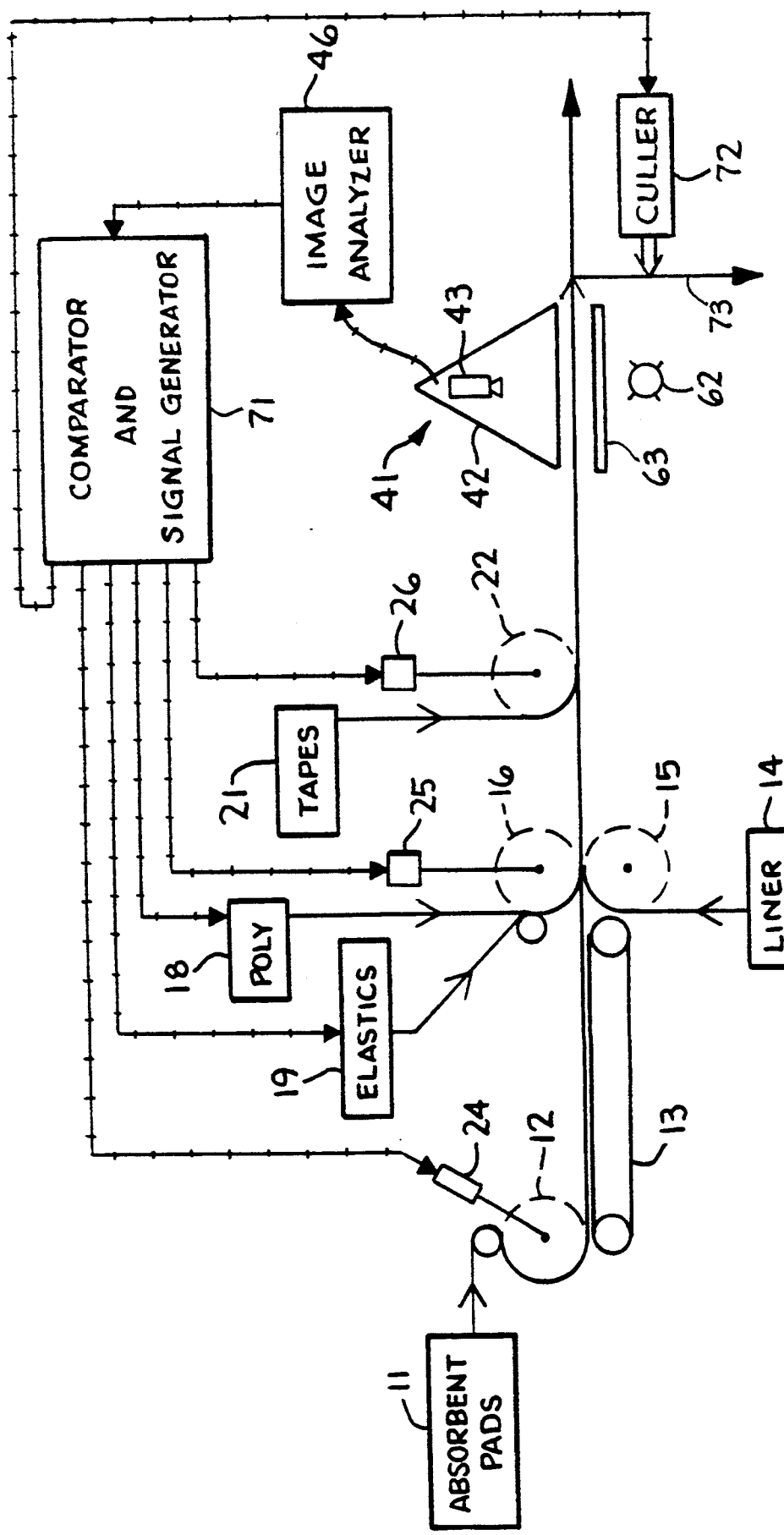
FIG. 3 is a schematic presentation of a second, preferred embodiment of the apparatus of the present invention.

In an alternative embodiment of the present invention depicted in FIG. 3, a backlighting light source 62 and a light diffuser 63 are disposed on the opposite side on the composite web from camera 43. Diffuser plate 63 provides for proper diffusion of light from the backlighting light source 62 such that a substantially constant intensity of light is created across the area of the web being inspected. In this embodiment, those components of the composite web which are opaque or are substantially opaque, will produce dark zones in the electronic image produced by camera 43. Those areas of the web which are relatively translucent will appear as light zones.

Ultraviolet light sources 44 and 45 or backlighting light source 62 are preferably strobed at a rate directly proportional to the rate at which the web travels along the machine direction of the fabrication system whereby the products contained in the web are effectively "stopped" for registration inspection. Where camera 43 is a high shutter speed camera, the shutter speed can be synchronous to the strobe such that the shutter is open upon each strobe of light sources 44 and 45 or light source 62.

Camera 43 preferably contains an array of photodiodes positioned to detect the light reflected from or transmitted through the web to camera 43. In one embodiment of the present invention, the effective size of the photodiode array is 256 vertical columns by 240 horizontal rows. This pattern divides each incoming image into 61,440 units known as pixels. In another embodiment, the effective size of the photodiode array is 512 vertical columns by 240 horizontal rows, providing 122,880 pixels. In these embodiments, the photodiodes are able to produce any one of 256 "gray scale" values corresponding to the amount of light received by that pixel, a low gray scale value representing a low amount of light.

Image-analyzing means 61 can be any suitable programmable computer. For example, the VIDEK RM1000 Vision Controller can be used as an image-analyzing means 61. The VIDEK RM1000 is able to perform linear measurements and real time image enhancements on signals generated by the photodiodes. These measurements can then be compared to a predetermined set of manufacturing tolerance levels for the purpose of determining whether the discrete product being inspected falls within acceptable manufacturing tolerances. Image-analyzing means 61 produces an electrical output signal for each such comparison, with the output signals being transmitted to control signal generator 70. Control signal generator 70 can be any suitable type of controller, either of the analog type or of the digital type. When a programmable digital computer is to be employed to generate the control signals, it can be separate from comparator 61 or a single such computer 71 (as in FIG. 3) can be employed to accomplish both the function of comparison and the function of control signal generation. In the right environment, a single digital computer can be employed to accomplish the functions of image analyzer 46, comparator 61 and control signal generator 70. However, it may be desirable for at least some of the control signals to be in analog form.

In one embodiment of the present invention, control signal generator 70 produces two distinct sets of output signals. The first set of output signals represents the numerical representation (in inches, millimeters, or pixels) of the variation in position of each component of the particular composite article from its predetermined desired position. The variance signals for a particular component position in a series of successive articles can then be averaged to produce a trend signal, which indicates the existence of any movement trend for that particular component position. These trend signals can be utilized to control one or more of the mechanisms which supplies the respective components to the fabrication line. In addition, these signals can be stored and subsequently downloaded for review.

The second set of signals represents a series of "on" or "off" signals generated as a result of the comparison of the actual component position with the desired component position. Each component of the composite web analyzed by apparatus 10 for its position in the machine direction can be in one of five conditions: (1) acceptable; (2) marginally forward; (3) marginally retarded; (4) unacceptably forward; or (5) unacceptably retarded. Similarly each element of the composite web analyzed by apparatus 10 for its position in the transverse direction can be in one of five conditions: (1) acceptable; (2) marginally to the left; (3) marginally to the right; (4) unacceptably to the left; or (5) unacceptably to the right. With regard to the second set of output signals, control signal generator 70 produces no signal when the respective web component is in an "acceptable" position. If a particular component is marginally retarded, a marginally retarded "on" signal will be generated by control signal generator 70 with respect to the particular component. A marginally forward "on" signal indicates that a one increment adjustment forward of the appropriate supply mechanism is necessary. A marginally forward "on" signal is generated when a particular element is marginally forward, causing a one increment retarded adjustment with respect to the element. Comparable "on" signals are created when an element is marginally left or marginally right. If a particular element is unacceptably retarded, the second set of output signals produces an unacceptably retarded "on" signal. Such an unacceptably retarded "on" signal indicates that a one increment adjustment forward of the appropriate component supply mechanism is necessary, as described above. In addition, the unacceptably retarded "on" signal indicates that the unacceptable composite article should be removed from the fabrication line without further processing. This can be accomplished in the embodiment of FIG. 3 by culler 72 diverting the unacceptable article from the fabrication line to a cull disposal line 73 in response to the receipt of a cull signal from comparator and signal generating means 70.

In the embodiment of the invention depicted in FIG. 1, motors 24, 25, and 26 and supply mechanisms 18, 19, and 21 are connected to receive output signals from control signal generator 70. When waist elastic bands 38a and 38b and leg elastic bands 38c and 38d are within their acceptable positions, control signal generator 70 does not deliver an "on" signal to motor 19, thereby maintaining the current orientation of the elastic bands. However, when the placement of waist elastic band 38a or 38b is marginally forward or marginally retarded from their acceptable positions, or when the placement of leg elastic band 38c or 38d is marginally to the left or marginally to the right from their acceptable positions, control signal generator 70 delivers an "on" signal to the elastic band supply mechanism 19 to effect a one increment phase shift with respect to the application of the respective pair of elastic bands.

In one embodiment of the present invention, optical brighteners are incorporated at the terminal ends of continuous web elements of the composite article. In this way, a splice from one roll to a subsequent roll of the continuous web element can be detected by the apparatus of the present invention. It is desirable that the finished product containing such a splice be culled from the fabrication line as an unacceptable product.

Comparator 61 and control signal generator 70 are preferably designed to average conflicting signals which occur simultaneously for a given supply mechanism, such as a "marginally forward" signal for waist elastic band 38a and a "marginally retarded" signal for waist elastic band 38b. If the conflict persists, the control signal generator 70 can activate an alarm signal to inform the operator of the problem. When the position of elastic bands 38 are unacceptable, control signal generator 70 delivers an "on" signal to supply mechanism 19 in order to effect a one increment phase shift for the respective pair of elastic bands and also transmits a culling signal to culler 72 which then removes the defective product from the fabrication line.

The magnitude of a single increment of control action can vary from component to component within a particular composite article and from one type of composite article to another type. Thus, it is desirable to employ supply mechanism controllers which are adjustable in order to accommodate changes in production practices. Where the supply mechanism controllers can be continuously varied, the first set of output signals (either original or averaged) can be transmitted to the supply mechanism controller to effect the desired variation in the supply of the respective component.

Due to the linear displacement along the machine direction of the supply mechanisms from image-producing means 41, control signal generator 70 is preferably programmed to take the respective lag time into consideration in the establishing of the respective control signal. A lag time corresponds to the time it takes for an adjustment in a respective supply mechanism to affect the position of the respective component in the composite article which is being inspected by image-producing means 41.

In order to avoid frequent adjustments to the supply mechanisms, it is preferred that control signal generator 70 "average" or "trend" a predetermined number of composite articles, and utilize such averaged values to signal changes to the supply mechanisms. For example, rather than causing a phase shift in response to each composite article which is outside the "acceptable" range, control signal generator 70 can "trend" a predetermined number of inspected composite articles and cause a phase shift only if the average position of a particular element is outside the "acceptable" range. This feature prevents undue phase shifts and reduces wear on the system.

Although the present invention has been disclosed herein with respect to preferred embodiments, it will be apparent to one of ordinary skill in the relevant art that various and further modifications may be made without departing from the true spirit and scope of the invention. The present invention can be used on either a continuous web fabrication system as illustrated in the drawings or a discrete unit fabrication system wherein all of the components are provided to the fabrication line in discrete form. While the positional relationships of the components have been described in terms of locations in the machine direction or locations in the transverse direction, the positional relationship can be at an angle to the machine direction other than 90°. Thus a combination of measurements in both the machine direction and the transverse direction can determine the position of a component at any desired angle with respect to a reference point. Such registration inspection can be performed with respect to each article or only for selected articles as they move in the machine direction past the image detector.

I claim:

1. An apparatus for fabricating a composite article from a plurality of components so that selected components thereof have positional relationships within acceptable ranges, the apparatus comprising:
   a fabrication line with a machine direction and a transverse direction, the fabrication line comprising a supply of each of said plurality of components, means for withdrawing a first one of said plurality of components from its supply and depositing it at a first point in said fabrication line, means for moving the thus deposited first component along the machine direction of the fabrication line, means for withdrawing a second one of said plurality of components from its supply and adding the thus withdrawn second component to the first component at a second point in said fabrication line downstream of said first point to form an in-process article, and means for withdrawing each of the remaining components from the respective supply thereof and sequentially adding it to a previously formed in-process article to form a new in-process article until all of said plurality of components have been added, thereby forming a composite article;
   means for creating a two-dimensional image of the composite article at a single station in said fabrication line, said means for creating a two-dimensional image comprising a high shutter speed camera having a matrix of photodiodes disposed therein whereby said matrix of photodiodes electronically produces a still picture image of said composite article;
   means for analyzing at least portions of said electronically produced still picture image to establish the location of at least one edge of at least one of said selected components in said composite article with respect to the transverse direction of said composite article in said fabrication line and to establish the location of at least one edge of at least one of said selected components in said composite article with respect to the machine direction of said composite article in said fabrication line;
   means for comparing each of the thus determined locations to a respective predetermined desired location to determine any variation between the respective determined location and the respective desired location;
   means for generating a control signal responsive to any thus determined variation which is outside of the acceptable range for the location of the respective component; and
   means for utilizing each thus generated control signal to control the addition of the respective component to the in-process articles on the fabrication line to promote the actual position of the respective component in subsequently produced composite articles being within its acceptable range.

2. Apparatus in accordance with claim 1 wherein said means for creating further comprises a radiation source positioned adjacent said fabrication line at said single station to provide illumination for said camera.

3. Apparatus in accordance with claim 2 further comprising means for strobing said radiation source at a rate directly proportional to the rate at which the composite article travels along the machine direction.

4. Apparatus in accordance with claim 3 wherein said radiation source is an ultraviolet light source mounted on the same side of said article as said camera, whereby the ultraviolet light activates optical brighteners incorporated into preselected components of said composite article such that said camera produces an image of said preselected components of said composite article.

5. Apparatus in accordance with claim 4 wherein said means for analyzing further comprises a programmable digital computer for analyzing at least portions of said electronically produced still picture image to establish the locations of at least one edge of each of said selected components in said composite article.

6. Apparatus in accordance with claim 5 wherein said means for utilizing each thus generated control signal to control the addition of the respective component comprises a phase shifting means which responds to the control signals to control the relative phases of addition of said components.

7. Apparatus in accordance with claim 1 wherein said means for utilizing each thus generated control signal to control the addition of the respective component to the in-process articles on the fabrication line comprises means for averaging a sequentially produced plurality of the thus generated control signals for a respective component to obtain a trend signal, and means for employing the trend signal to control the addition of the respective component to the in-process articles on the fabrication line to promote the actual position of the respective component in subsequently produced composite articles being within its acceptable range.

8. A method for fabricating a composite article from a plurality of components so that selected components thereof have positional relationships within acceptable ranges, the method comprising the steps of:
  withdrawing a first one of said plurality of components from a supply thereof at a first point in a fabrication line and passing the first one along the machine direction of the fabrication line;
  withdrawing a second one of said plurality of components from a supply thereof and adding the second one to the first one to form an in-process article;
  withdrawing the remaining components from the respective supplies thereof and adding the remaining components at subsequent points in the fabrication line to the previously formed in-process article to form a new in-process article until all of said plurality of components have been added, thereby forming a composite article;
  creating a two-dimensional image of the composite article at a single station in said fabrication line using a high shutter speed camera having a matrix of photodiodes disposed therein said matrix of photodiodes electronically produces a still picture of said composite article;
  analyzing at least portions of said electronically produced still picture image to establish the location of at least one edge of at least one of said selected components in said composite article in the transverse direction and to establish the location of at least one edge of at least one of said selected components in said composite article in the machine direction;
  comparing each of the thus determined locations to a respective predetermined desired location to determine any variation between the respective determined location and the respective desired location;
  generating a control signal responsive to any thus determined variation which is outside of the acceptable range for the location of the respective component; and
  utilizing each thus generated control signal to control the addition of the respective component to the in-process articles on the fabrication line to promote the actual position of the respective component in subsequently produced composite articles being within its acceptable range.

9. A method in accordance with claim 8 wherein the step of utilizing each thus generated control signal to control the addition of the respective component to the in-process articles on the fabrication line comprises averaging a sequentially produced plurality of the thus generated control signals for a respective component to obtain a trend signal, and employing the trend signal to control the addition of the respective component to the in-process articles on the fabrication line to promote the actual position of the respective component in subsequently produced composite articles being within its acceptable range.

10. A method in accordance with claim 8 wherein at least one of said components is a continuous web and each composite article is a segment of the resulting composite web.

11. A method in accordance with claim 10 further comprising placing optical brighteners on predetermined components, said optical brighteners having the ability to produce light in the visible wavelength range in response to excitation by ultraviolet light; and wherein the step of creating a two-dimensional image of a composite article comprises illuminating a segment of said composite web with ultraviolet light, whereby said image indicates the position of the components containing the optical brighteners.

12. A method in accordance with claim 10 wherein at least one of said selected components is supplied to the fabrication line as a discrete object.

13. A method in accordance with claim 8 further comprising:
  generating an article cull signal when the location of at least one component of said composite article is not within its predetermined acceptable range; and
  culling said composite article from the fabrication line in response to the generation of the article cull signal.

14. A method in accordance with claim 8 further comprising storing each of the thus generated control signals whereby the thus stored signals can be subsequently downloaded for review.

15. A method in accordance with claim 8 wherein said composite article is a disposable absorbent article.

16. A method in accordance with claim 8 wherein said composite article is a diaper and the components whose location is being determined include an absorbent pad, leg elastic elements, waist elastic elements, and tape elements.

17. A method in accordance with claim 8 wherein said composite article is an incontinence device and the components whose location is being determined include an absorbent pad, leg elastic elements, and waist elastic elements.

18. A method in accordance with claim 8 wherein said step of creating a two-dimensional image comprises providing a radiation source adjacent to said single station to provide illumination of the composite article in said single station, and strobing said radiation source at a rate directly proportional to the rate at which the composite article in said single station travels along the machine direction.

* * * * *